United States Patent [19]
Pollard

[11] Patent Number: 4,594,883
[45] Date of Patent: Jun. 17, 1986

[54] MONITORING PHYSICAL PROPERTIES OF A FLUID

[75] Inventor: Geoffrey J. Pollard, Newport Pagnell, England

[73] Assignee: The British Hydromechanics Research Assoc., Cranfield, England

[21] Appl. No.: 684,926

[22] PCT Filed: May 3, 1984

[86] PCT No.: PCT/GB84/00149
§ 371 Date: Dec. 21, 1984
§ 102(e) Date: Dec. 21, 1984

[87] PCT Pub. No.: WO84/04388
PCT Pub. Date: Nov. 8, 1984

[30] Foreign Application Priority Data
May 3, 1983 [GB] United Kingdom ............... 8312071
Nov. 3, 1983 [GB] United Kingdom ............... 8329334

[51] Int. Cl.⁴ .......................................... G01N 11/14
[52] U.S. Cl. ........................................................ 73/54
[58] Field of Search ............................. 73/59, 60, 54

[56] References Cited
FOREIGN PATENT DOCUMENTS

| | | |
|---|---|---|
| 1698118 | 1/1972 | Fed. Rep. of Germany . |
| 7400437 | 8/1975 | France ................................ 73/54 |
| 95389 | 9/1960 | Netherlands ...................... 73/59 |
| 1295617 | 8/1972 | United Kingdom . |

Primary Examiner—Stewart J. Levy
Assistant Examiner—Joseph W. Roskos
Attorney, Agent, or Firm—Irvin A. Lavine

[57] ABSTRACT

An impeller on a stirrer shaft is rotated at constant angular velocity by a motor within a chamber. Vibrations induced in the shaft by virtue of the stirring action of the impeller are sensed by a transducer whose output is conditioned by equipment from these signals. The invention can be applied to processes in a reaction vessel and liquid in a pump chamber. Since the excitation is a constant angular velocity and the induced effect is vibration, there is no interference between excitation and induced effect although the transducer is mounted on the stirrer shaft.

10 Claims, 7 Drawing Figures

MONITORING PHYSICAL PROPERTIES OF A FLUID

FIELD OF THE INVENTION

The invention relates to a method and apparatus for measuring properties of a fluid material within a chamber enclosing impeller means mounted on a stirrer shaft extending into the chamber. In particular, it relates to a method and apparatus for monitoring the properties and flow characteristics of such a material as it is being agitated within a reaction vessel enclosing impeller means mounted on a stirrer shaft extending into the reaction vessel and, optionally, thereby controlling the processes taking place within the vessel.

BACKGROUND ART

Various forms of known apparatus use vibratory methods to measure properties such as viscosity of a material. These all operate on the general principle of bringing the said material into contact with a member, generating and possibly maintaining vibrations on this member by exciting means, detecting the influence of said material on the characteristics of these vibrations and of inferring properties of said material by analysis of this influence on the characteristics of the vibrations. The exciting means for generating and possibly maintaining vibrations do not include the material under test but rather the material only influences the characteristics of vibrations generated by other means and in general these exciting means are located separately from said material. In many cases the material is contained within a sealed chamber and the exciting means are attached to the vibrating member on the outside of the chamber. In general, the vibrations generated on the member by the exciting means are chosen to occur at a limited number of well-defined frequencies. GB-A 1295617 is an example of such known apparatus. Vibrations are induced in a paddle by an electromagnet acting on an arm connected to the paddle by means of a spring and the vibrations induced are detected by a further electromagnet connected to a further arm forming an extension of the first arm on the other side of the spring. The electromagnets and the arms are contained within a sealed housing, the spring extending through a sealable connection to the paddle. The apparatus is designed to operate at the specific natural resonant frequencies of the vibrating system.

Known apparatus as described above is unsuitable for measuring properties of a process material either as it is being agitated within a stirred vessel or as it is being pumped through a pump housing, for two main reasons. Firstly, the vibrating member would be excited, not only by the external means, but also by the flow of the material within the vessel or the pump and this would swamp the vibrations generated by the external means, making it difficult to detect the influence of said material on the characteristics of these externally-generated vibrations, hence making it difficult to infer properties of said material. Secondly, sealing means would be required around the apparatus as it pierces the wall of the vessel or pump and this would be a serious disadvantage in most cases involving materials that are either hazardous or must remain sterile. Known apparatus for use in stirred vessels comprise non-vibratory sensors such as thermometers, pH probes and dissolved-oxygen probes and such sensors are used as a means of monitoring and, optionally, controlling the process more effectively with the aim of improving either the process yield or the quality of the finished product. While these devices may proved adequate within certain process regimes, they may be insensitive to some changes in material properties that have a major influence on yield and product quality. Such non-vibratory sensors also suffer from the drawback of requiring sealing means where they enter a fully-enclosed vessel. Many batch processes within stirred vessels; for example resin manufacture, polymerisation and biotechnology reactions; undergo significant changes in viscosity through the batch and viscometry is therefore a potentially useful means of monitoring and, optionally, controlling the process. However, current techniques for this purpose include either sampling the material and using instruments such as rotating cups or U-tubes or pumping the material to a sealed rotating-cup device. The former practice is time-consuming for repeated measurements and requires a leak-proof sampling mechanism while the latter suffers from possible problems of clogged pipework and cross-contamination between batches.

Viscometry at non-ambient temperatures, whether the material has been sampled from a stirred vessel or not, is difficult or inconvenient using existing means, because the whole of the apparatus in contact with the material must be maintained at the required temperature.

While in some instances it might be possible to infer changes in viscosity from corresponding changes in power absorbed by the material (at a constant rotational speed), this is only possible at low and intermediate values of Reynold's number, in which viscous forces are significant. Thus, known art includes means to measure the absorbed power, either by recording the current drawn by the driving motor or by recording the torque on the shaft of by some other means, and hence infer changes in viscosity at low and intermediate values of Reynold's number. GB-A-764 850 for example describes measurements taken with a driving member which can be constantly rotated. However these measurements are not taken from the driving member during its constant rotation: they are either taken from a separate measuring member or from the driving member when it is no longer driven at constant speed.

At high Reynold's number, where interia forces predominate over viscous forces, little or no change in power at constant speed can be detected as viscosity varies. Since many stirred vessels operate at high Reynold's number (to achieve the turbulence required to enhance mixing), there is a clear need for means and apparatus to monitor viscosity changes in this region.

DISCLOSURE OF THE INVENTION

It is an object of the present invention to improve known methods of measuring properties of a material from induced vibrations by using the material under test as the means of generating the vibrations, the characteristics of these vibrations being used to infer properties of the material.

It is a possibility with the present invention to improve known methods of measuring properties of a material by sensing vibrations over a wide spectrum of frequencies rather than a few, well-defined frequencies.

The invention can be applied to apparatus and methods for measuring properties, for example viscosity, of a process material as it is being agitated within a stirred vessel, or as it flows through a pump. When applied to stirred vessels the invention both improves on known art (employing measurement of absorbed power) applying to intermediate Reynold's number and also provides a method applying to high Reynold's number where this known art does not apply. The invention can be applied to measuring viscosity or other properties of the material under conditions of non-ambient temperature or pressure, or under other non-ambient conditions.

The invention therefore provides, in order to measure the properties of a material within a chamber apparatus as set out in claim 1 or a method as set out in claim 7 of the claims of this specification. Moreover, apparatus according to the invention, for controlling a process, may be obtained by providing control means for varying operation of the process in accordance with information on process conditions detected by the transducers.

Where it is more convenient to do so, the transducers may be disposed outside the chamber. This reduces sealing difficulties.

A method of controlling a process comprises a method of the invention as set out above in which operation of the process is varied in accordance with information provided by analysis of the signals representing vibration of the stirrer shaft.

The impeller means within the chamber generate flow in the material being processed and this promotes any desired chemical and/or physical reaction. However, flow so generated also results in significant mechanical loads on the stirrer shaft, including torsional loads associated with absorbed power and vibrational bending loads.

Analysis of shaft vibration, such as bending vibration or torsional vibration, provides information from which details of flow of fluid may be deduced, thus providing information about fluid conditions. This allows the stirrer shaft to be used as a form of anemometer in which flow characteristics are inferred from vibration measurements.

Where the sensors are disposed outside the chamber, use of the shaft as an anemometer precludes any sealing problems that might arise, other than those already existing with the stirrer shaft, if other sensor equipment was employed within the chamber. The use of the shaft as an anemometer also means that flow characteristics are measured at a well defined location within the chamber, generally along the chamber axis. Flow measured elsewhere in the chamber may be untypical of gross characteristics and may vary more from one installation to another.

A wide range of transducers may be used to measure shaft vibration. However, in a preferred embodiment of the apparatus according to the invention, strain gauges are cemented onto the shaft and the signals generated by these transducers are transmitted from the shaft by telemetry equipment.

The output from the device analysing shaft vibration may be used to provide a direct input to existing control systems. Moreover, since shaft loads are measured, the mechanical reliability of the drive may be simultaneously monitored and incipient failure predicted.

A technique of monitoring the bending vibration of the stirrer shaft exploits the fact that shaft vibration is caused and governed by flow characteristics within the chamber which are also the main factors controlling process yield, efficiency and product quality. Where the technique involves applying measuring instruments to the shaft outside the chamber, no additional seals are required beyond those already in use on the shaft.

The analysis of shaft vibration is preferably carried out in terms of its spectral characteristics in addition to its overall level. The spectral characteristics of shaft vibration are preferably specified in terms of precessional spectra in which positive frequencies represent anticlockwise precession and negative frequencies represent clockwise precession.

The analysis of shaft vibration is preferably carried out automatically by instrumentation that can act to provide an input to existing automatic control systems. Apparatus according to the invention may thus consist of a microprocessor-based instrument dedicated to the task of accepting the vibration signals as input and presenting the spectral characteristics and overall vibration levels as output.

In one particular embodiment of the invention, the kinematic viscosity of the fluid is obtained by correlating this kinematic viscosity with the characteristics of shaft vibration. In this case, it is necessary to calibrate the apparatus by recording kinematic viscosity along with shaft vibrational loads through a trial batch cycle. Once this calibration is complete, kinematic viscosity may be inferred from measurements of shaft vibration. The characteristics of shaft vibration used for correlation with kinematic viscosity may vary from one application to another, depending on the type and arrangement of mixing equipment used and on the particular process involved.

As an example of the use and interpretation of these precessional spectra, the relative intensities of bulk circumferential flow and turbulence have a major influence on reaction rates and yield, since turbulence promotes intimate mixing between the reactants whereas bulk circumferential flow does not. If the shaft is spinning about its own axis at N revolutions per second in an anticlockwise sense looking down, a peak representing bulk circumferential flow will appear at $-N$ hertz in the spectrum, whilst turbulence-excited shaft resonance will occur at $-(f+N)$ hertz and at $f-N$ hertz, where f is the first lateral resonant frequency of the shaft. Thus by comparing the signal power associated with the peak representing bulk circumferential flow and one of the peaks representing turbulence, an assessment may be made of the effectiveness of the process vessel as a generator of turbulence.

A further embodiment of the invention allows the in situ measurement of both density and viscosity of process liquor or other material being processed. In this case, it is necessary to measure shaft torque as well as bending vibration. The technique relies on the fact that both bending and torsional loads are proportional to density at high Reynold's number, whilst bending loads also depend on viscosity. Thus, by measuring torque and bending vibration, it is possible to infer density and viscosity separately.

Examples of flow characteristics which have a strong influence on process performance and which may be controlled by means of the method and apparatus of the invention include:

(a) Swirl and Turbulence Intensities: Unless the vessel is properly baffled, the rotating impeller means tend to generate mainly circumferential flow which results in poor mixing. Baffles or other deflectors provided in the reaction vessel break up this swirl, generating turbulence and hence more intimate mixing. The effectiveness with which this occurs therefore has a profound effect on the process yield. Apparatus in accordance with the invention may be used to measure this effect through a spectral analysis of the bending vibration, since the two types of flow result in different spectral peaks.

(b) Changes in Fluid Properties: Some batch processes involve significant changes in the properties of a liquor, such as density and viscosity. These changes may be detected as alterations in either the overall bending vibrational loads or their spectral characteristics. Since such changes frequently occur at crucial stages in the batch cycle, apparatus analysing bending vibrations may be used as a means for controlling important system parameters such as shaft speed or gas flow rate.

(c) Gas Dispersion: Those processes involving the transfer of gas into a liquid depend for their efficiency on the effective dispersion of the gas throughout the vessel by the impeller. Radically different flow regimes are produced depending on whether the gas input or the impeller rotation is the dominating influence; optimum process results are achieved when these two factors roughly balance. These flow regimes may be identified using apparatus according to the invention, thereby allowing gas flow rate or shaft speed to be adjusted appropriately.

(d) Inadequate Mixing of Shear-Thinning Liquors: Thixotropic liquors frequently suffer from the problem of high shear and hence low viscosity in the vicinity of the impeller means, but low shear and high viscosity close to vessel walls. This leads to inadequate mixing of the liquor close to the wall, with serious repercussions on process results. This phenomenon, too, may be detected by means of apparatus according to the invention, thus permitting remedial action to be taken.

An embodiment of the present invention is hereafter described, by way of example, with reference to the accompanying drawings.

MODE FOR CARRYING OUT THE INVENTION

A water-based liquor 11 is prepared by mixing an additive liquid, sold under the trade name "Jeffox WL1400" with water. This additive liquid has the property that when mixed with water, the dynamic viscosity of the resultant water-based liquor can be readily varied by changing the concentration of the additive liquid in the water.

Figure 1:
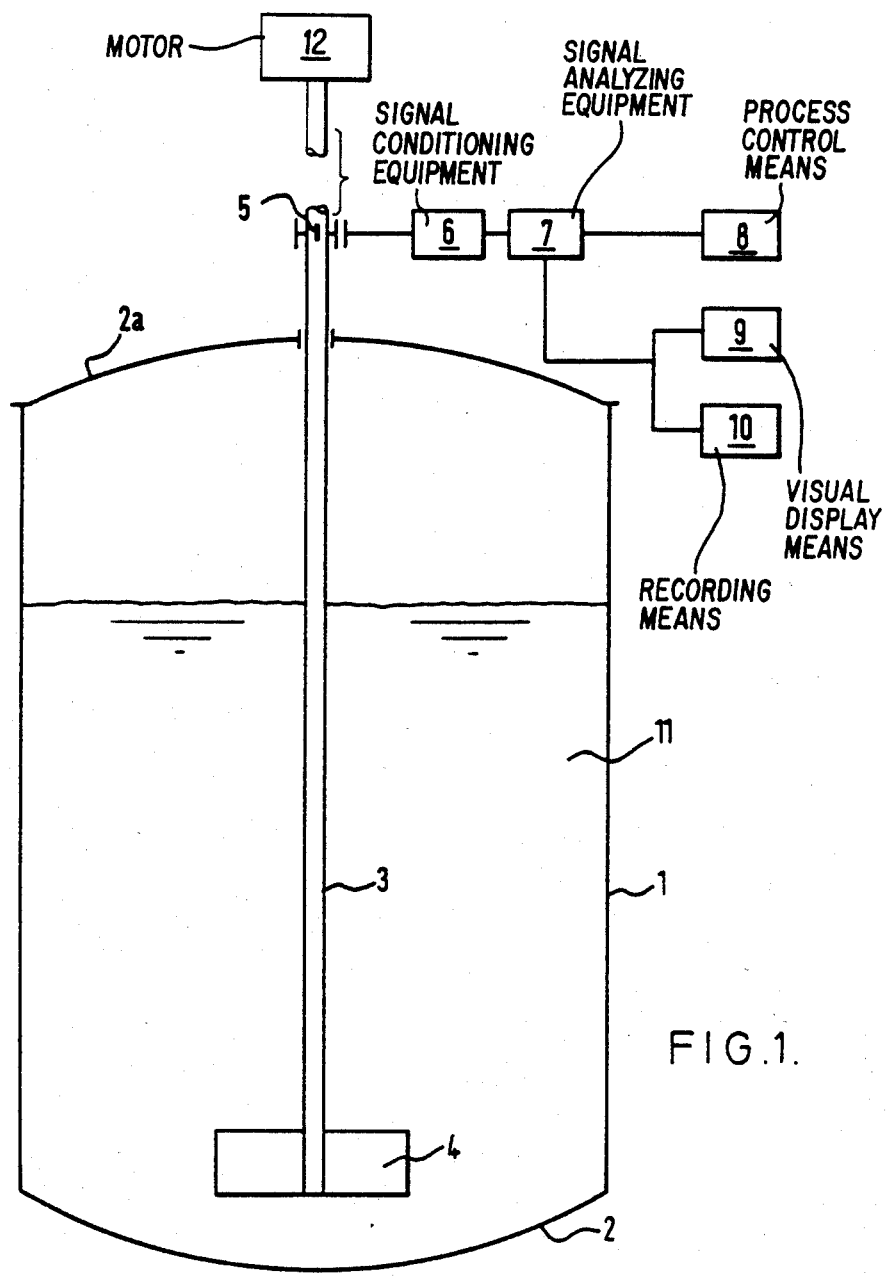
FIG. 1 is a schematic representation of monitoring apparatus, in accordance with the invention, for preparing batches of water-based liquor having accurately controlled viscosities for use in projects in which such liquors having accurately controlled viscosities are required.
Figure 2:
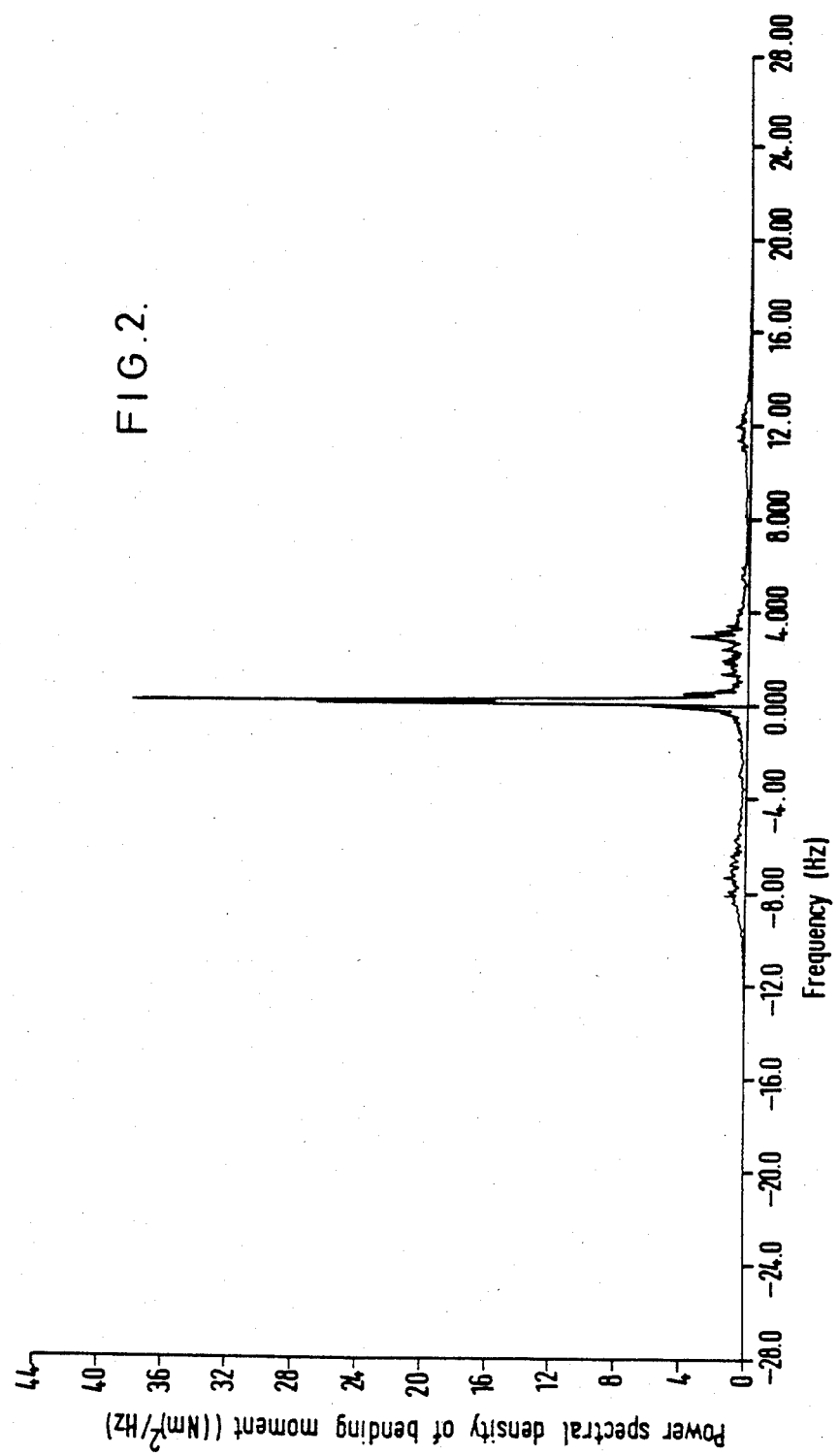
FIGS. 2 to 5 are graphic representations of precessional spectra for liquors having viscosities of 9, 15, 31 and 64 centistokes, respectively.
Figure 3:
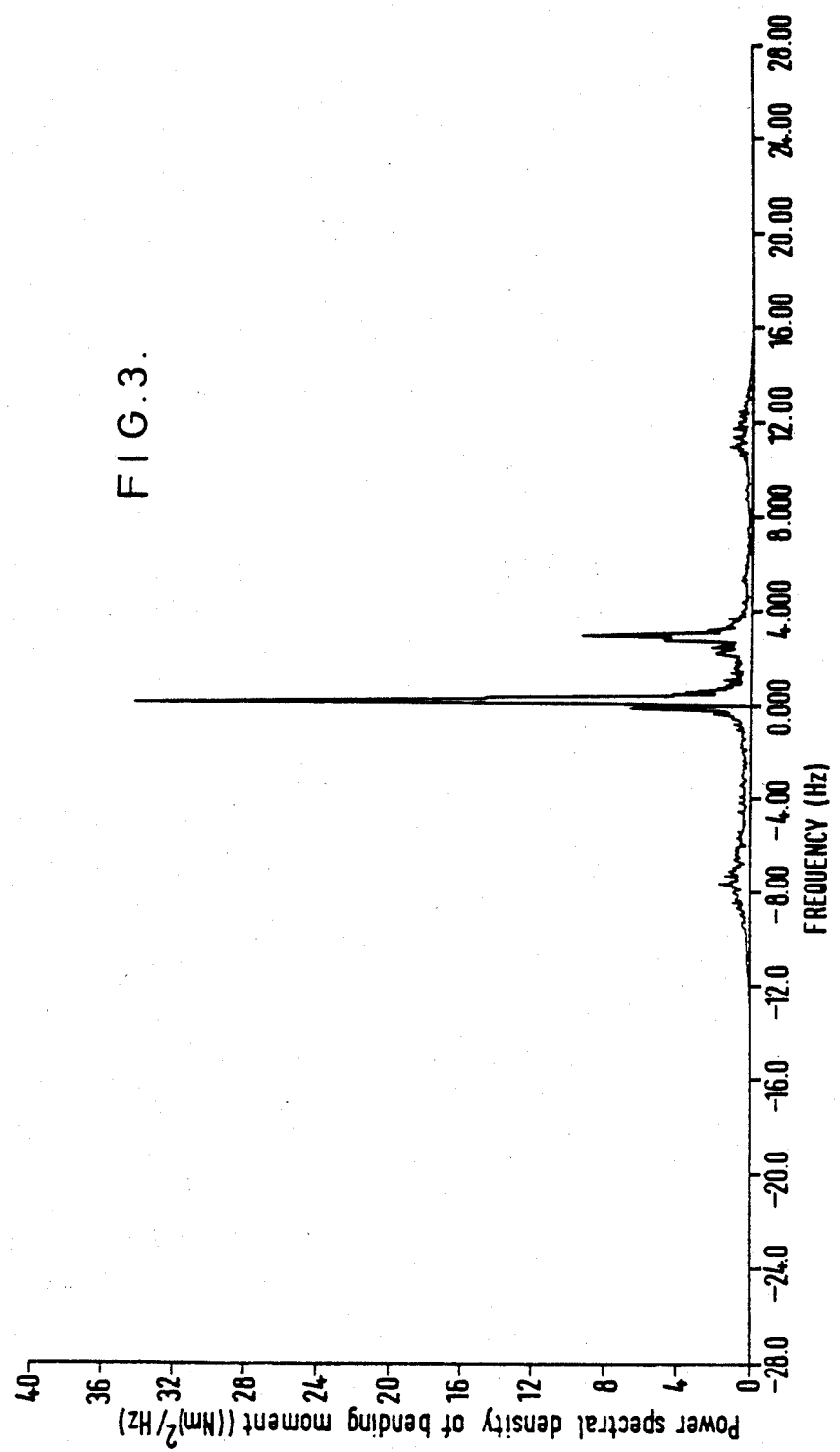
Figure 4:
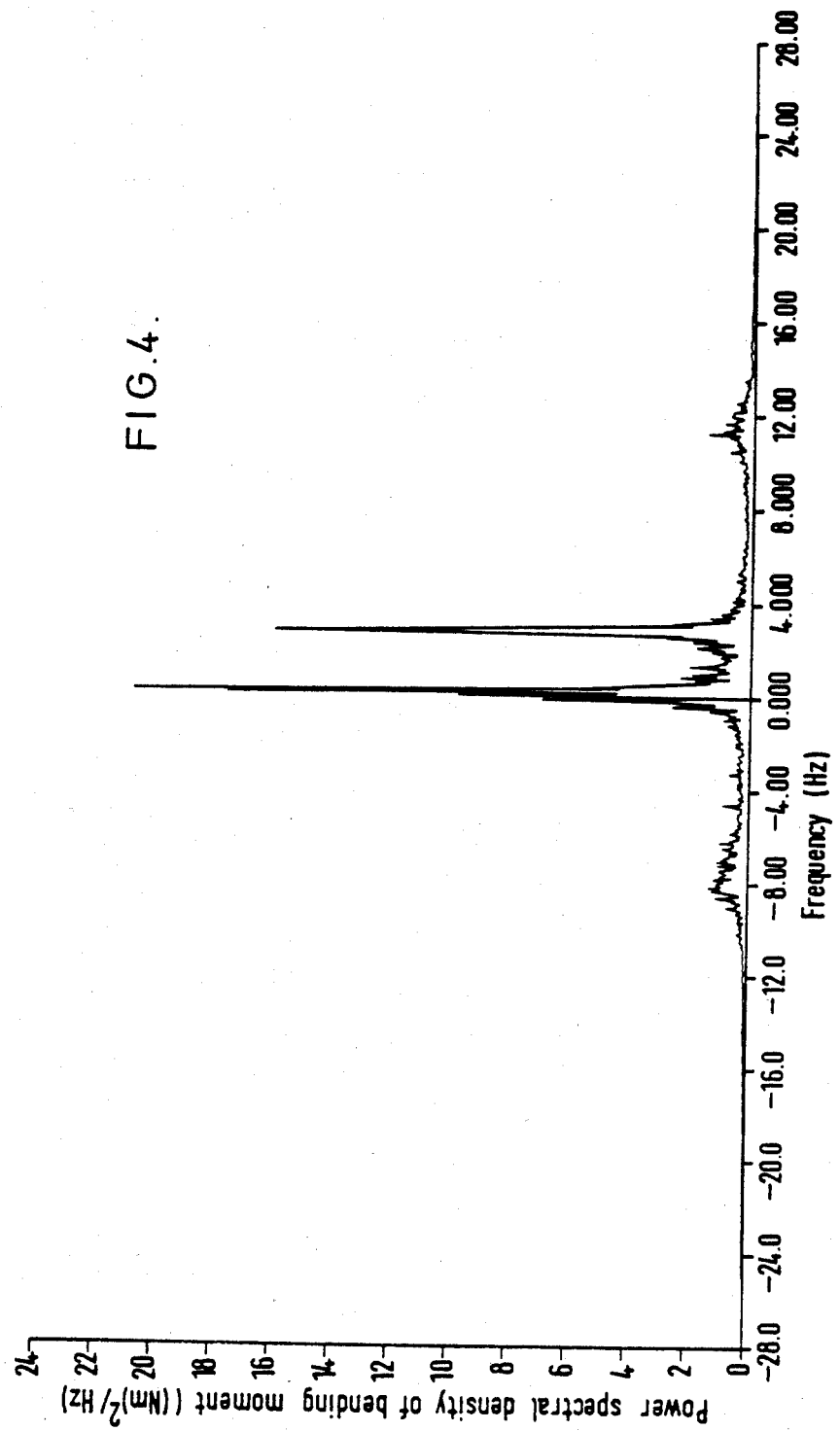
Figure 5:
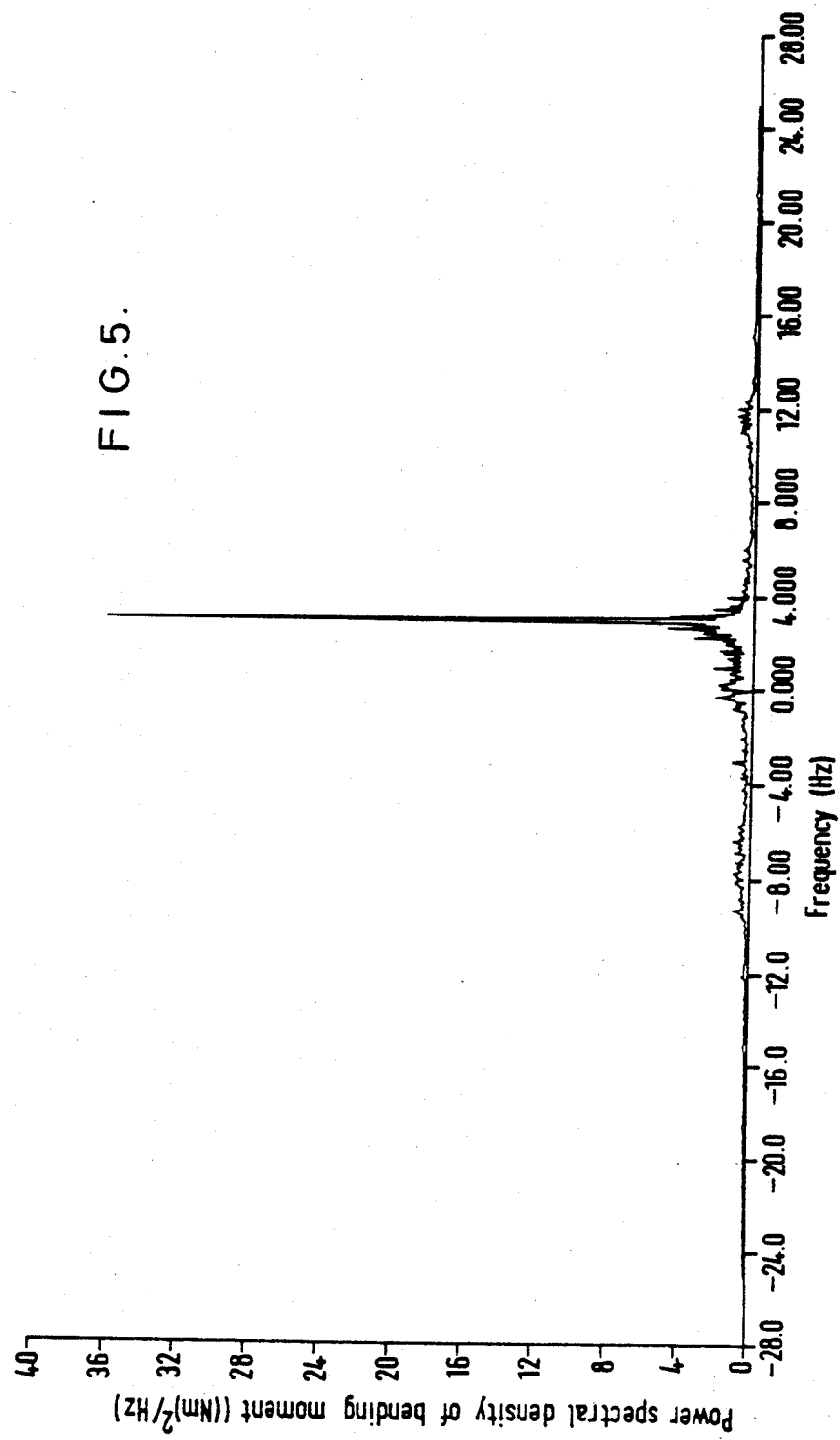

As shown in FIG. 1, apparatus for preparing batches of water-based liquor 11 having accurately controlled viscosities comprises a reaction vessel consisting of a cylindrical side wall 1 of 0.61 m internal diameter and a dished bottom 2 with a 0.61 m radius and contains a liquor 11 to a depth 0.61 m and a similar dished cover 2a.

The liquor 11 within the reaction vessel is agitated by means of an impeller 4 mounted on a shaft 3, installed concentrically with the reaction vessel, in such a position that the lower edges of the blades of the impeller 4 lie in the plane defined by the joint between the side wall 1 and dished bottom 2 of the reaction vessel. The cover 2a is sealed around the shaft 3. The impeller 4 has a diameter of 0.205 m and has six blades 0.068 m wide and mounted at intervals of 60° around the circumference of the shaft 3 with their planes perpendicular to the plane defined by the joint between the side wall 1 and the dished bottom 2 of the reaction vessel. The shaft 3 is in operation rotated at constant angular velocity by a motor 12.

Transducers in the form of strain gauges 5 are cemented on to the shaft 3 at a distance of 1.098 m along the axis of the shaft 3 from the lower edges of the impeller blades 4 to form two full Wheatstone bridges respectively along two mutually perpendicular axes of lateral vibration (hereafter referred to as the x- and y-axes). The two axes should be arranged to form a right-handed system when viewed from above. Each strain-gauge Wheatstone bridge is connected up to commercially available telemetry equipment (such as equipment sold under the trade name "Astech") which transmits the signals from the two Wheatstone bridges on the shaft 3 and presents them in the form of analogue voltages.

These two signals are then fed through signal conditioning equipment 6 and from the signal conditioning equipment 6 to signal analyzing equipment 7. Signals embodying information from the analyzing equipment 7 are fed to process control means 8 and to visual display means 9 and/or recording means 10.

The dynamic viscosity of the liquor 11 is varied by changing the concentration of the additive liquid in water and at each kinematic viscosity produced, by concomitant variations in dynamic viscosity and density of the mixture, precessional spectra are recorded and analysed by the signal analysing equipment 7.

The signal analysing equipment 7 preferably takes the form of a microprocessor-based instrument to automatically carry out the necessary analysis. With this arrangement, the two signals are read into a complex array which is used as input in the standard Fast Fourier Transform (FFT) routine; the x-axis signal is read into the real part of the array and the y-axis signal into the imaginary part of the array. This differs from the common use of the FFT routine, in which one signal only is used as input into the real part of the array.

When processed by the FFT routine, the first half of the complex array contains amplitudes for positive frequencies, and the second half contains amplitudes for negative frequencies. The resulting spectrum covering both positive and negative frequencies is, in general, asymmetric about the zero hertz line; i.e. the signal power at any positive frequency will not necessarily be equal to the signal power at the corresponding negative frequency of the same absolute value. This differs from the result of the common use of the FFT routine referred to above, in which the resulting spectrum is always symmetric about zero hertz.

In the asymmetric spectrum, which is referred to as the precessional spectrum, positive frequencies request anticlockwise precession of the shaft and negative frequencies clockwise precession. Each positive or negative frequency may be related to a particular type of flow within the process vessel, which in turn has a major influence on process conditions and results.

Four such spectra are illustrated by way of example in FIGS. 2 to 5, corresponding to liquor viscosities of 9, 15, 31 and 64 centistokes, respectively. These show that the bending moment imposed on the shaft 3 by the liquor 11 is high at two main frequencies: at approximately 0.2 Hertz and at approximately 3 Hertz, the latter corresponding to the shaft rotational speed of three revolutions per second (these frequencies being those measured in the rotating frame of reference of the shaft). FIGS. 2 to 5 also show that the magnitude of the bending moment at each of these frequencies depends on the viscosity of the liquor 11. Hence, the analysis of precessional spectra in this case takes the form of finding the root-mean-square (r.m.s.) bending moment associated with each of these frequencies. For this purpose, the band width of each of the two frequencies is defined as ±0.488 Hertz, centred on the frequency at which power density reaches a maximum. The r.m.s. bending moment for each frequency is then found by integrating the curve across this band width and by taking the square root of the result. The r.m.s. bending moments found by the analysing equipment 7 are a measure of the viscosity of the liquor 11 and, in use, the apparatus must first be calibrated by obtaining readings of r.m.s. bending moments for liquors having a range of viscosities.

Figure 6:
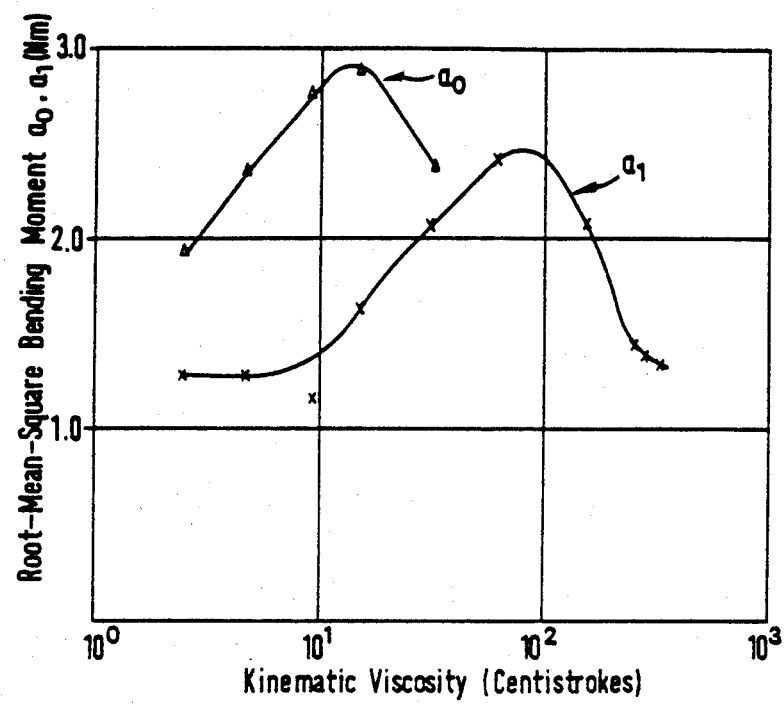
FIG. 6 is a graphic representation of the relationship between the viscosity of the liquor and the root mean square of the bending moments in the shaft of the apparatus shown in FIG. 1 at two frequencies of vibration: 0.2 Hertz and 3 Hertz, approximately, these frequencies being taken to have a bandwidth of ±0.488 Hertz.

FIG. 6 acts as a calibration cure for the device and shows the correlation obtained between the r.m.s. bending moments $a_0$ and $a_1$, respectively associated with frequencies of approximately 0.2 Hertz and 3 Hertz, and the liquor viscosity.

Figure 7:
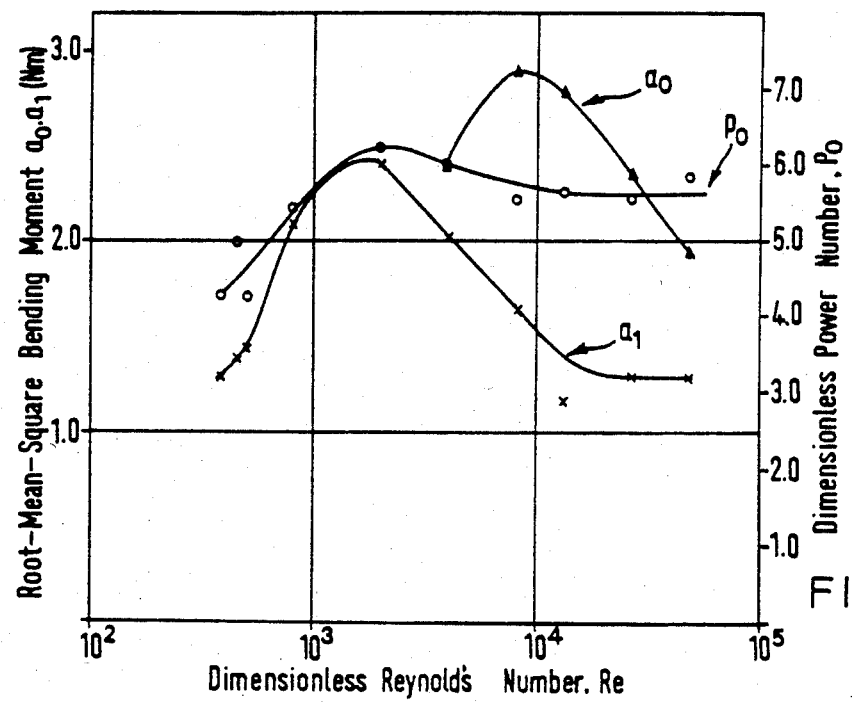
FIG. 7 is an adaptation and extension of FIG. 6, with Reynolds number plotted as the abscissa.

FIG. 7 includes a plot of the dimensionless Power Number, Po, in addition to curves of $a_0$ and $a_1$ which have already been presented in FIG. 6.

The Power Number is defined as $$P_o = \frac{P}{\rho N^3 D^5}$$

where
P is the power delivered to the process material and is equal to $2\pi N\tau$ where $\tau$ is shaft torque,
$\rho$ is material density,
N is shaft rotational speed in revs per second
and D is the diameter of the impeller.
The abscissa of the graph is Reynold's Number, (which is dimensionless) defined as $$R_e = \frac{\rho ND^2}{\eta} = \frac{ND^2}{\nu}$$

where $\eta$ is the dynamic viscosity and $\nu = \eta/\rho$ is the kinematic viscosity.

In FIG. 6, $a_0$ and $a_1$ are plotted against kinematic viscosity, $\eta$, measured is centistokes whereas in FIG. 7 these values and Po are plotted against Reynold's Number. Since Re is inversely proportional to $\nu$, the curves of $a_0$ and $a_1$ in FIG. 7 are the reverse of those in FIG. 6.

FIG. 7 illustrates the advantages of measuring bending loads ($a_0$ and $a_1$) over measuring torque (presented in the form of Po). Thus at high Reynold's Number, say higher than $10^4$, Po is essentially constant; i.e. is independent of Re and (since N and D are constant) of $\nu$, while the plot $a_0$ of r.m.s. bending moment varies dramatically in this region. However, from the definition of Po, since Po is a constant in this region of high Re, the power P is given by $$P = \text{constant} \cdot \rho N^3 D^5$$

i.e. is proportional to density. Therefore, measurements of P, either from measurement of $\tau$ or the motor current, may be used to infer $\rho$ but not $\nu$ in this region of high Re.

At intermediate values of Re (say $10^2$-$10^4$), Po is dependent on Re and hence $\nu$ and so measurements of $\tau$ or motor current might be used to infer $\nu$. However, it can be seen that the plot $a_1$ of r.m.s. bending moment is considerably more sensitive to changes in $\nu$ in this region than is Po.

The apparatus described both improves on this technique at intermediate Re and also provides a method at high Re where this technique does not apply.

It is envisaged that this preferred embodiment of the invention could be used for similar purposes such as blending oils, printing inks, clay and cement slurries or lubricant emulsions to obtain a blend having a precise viscosity.

The possibility noted above of inferring fluid density, $\rho$ from measurements of power (or torque) at high Reynold's Number is exploited in an extension of this embodiment in which fluid density and dynamic viscosity are measured simultaneously in this region of high Reynolds Number. By including a third wheatstone bridge of strain-gauges to monitor shaft torque, the density of the fluid may be determined provided that the power number, Po, at High Reynolds Number has been previously determined. Then by inferring kinematic viscosity, $\eta$, from measurements of bending moment as described above, dynamic viscosity, $\eta$ may be inferred from the relation $\eta = \nu\rho$.

The invention has been described above in connection with the monitoring of a liquid in a reaction vessel. It can however be applied to measurement of properties of a fluid within any chamber, for example a pump housing. These properties can be measured at non-ambient temperatures, pressures or other conditions by providing means to control these conditions within the chamber and its contents.

I claim:

1. Apparatus for the measurement of properties of a fluid comprising a chamber, a stirrer shaft extending into the chamber, impeller means on said shaft within said chamber, means to impart a constant angular velocity to said shaft and to said impeller means, and sensor means for detecting conditions within the chamber comprising:
   a. transducers for detecting vibration of the stirrer shaft during said constant angular velocity;
   b. signal conditioning equipment operatively connected to the transducers to provide signals representing vibration of the stirrer shaft; and
   c. analyzing equipment for receiving said signals for providing indications of the flow characteristics of liquid in said chamber based on said signals.

2. Apparatus according to claim 1 in which the transducers are disposed outside the chamber.

3. Apparatus according to claim 1 in which the transducers are mounted on said stirrer shaft.

4. Apparatus for controlling a process comprising apparatus according to claim 1, and control means for varying operation of the process.

5. Apparatus, according to claim 4, said control means connected to receive said signals from the analyzing equipment.

6. Apparatus, according to claim 4, and further comprising visual display means and/or recording means connected to the analyzing equipment to receive said signals therefrom.

7. A method of measuring properties of a fluid material within a chamber provided with at least one stirrer shaft extending thereinto and into the material therein, and the shaft supporting impeller means for movement within the fluid material, the method comprising the steps of rotating said stirrer shaft at constant angular velocity, and detecting vibration of said stirrer shaft by transducers, passing the output from the transducers to signal conditioning equipment, thereby to provide singals representing vibration of said stirrer shaft, and analyzing said signals to determine properties of the fluid material.

8. A method, according to claim 7, wherein the transducers are disposed outside the chamber.

9. A method, according to claim 7, and correlating the characteristics of bending vibration loads on said stirrer shaft with liquid viscosity.

10. A method of controlling a process, comprising a method according to claim 7, and varying the process in accordance with information provided by the analyzing equipment.

* * * * *